United States Patent [19]
Enterline

[11] Patent Number: 5,839,434
[45] Date of Patent: Nov. 24, 1998

[54] METHOD AND APPARATUS FOR DISPENSING RESPIRATORY GASES

[75] Inventor: Jack Joseph Enterline, Fort Pierce, Fla.

[73] Assignee: Invacare Corporation, Elyria, Ohio

[21] Appl. No.: 153,569

[22] Filed: Nov. 16, 1993

(Under 37 CFR 1.47)

[51] Int. Cl.$^6$ .................................................. A61M 16/00
[52] U.S. Cl. .............................. 128/204.23; 128/204.18; 128/204.24; 128/203.12
[58] Field of Search ................... 128/204.23, 203.22, 128/204.18, 205.24, 203.12, 204.21, 204.24, 204.26

[56] References Cited

U.S. PATENT DOCUMENTS

| | | | |
|---|---|---|---|
| 4,210,136 | 7/1980 | Apple | 128/204.21 |
| 4,414,982 | 11/1983 | Durkan | 128/716 |
| 4,457,303 | 7/1984 | Durkan | 128/204.24 |
| 4,461,293 | 7/1984 | Chen | 128/204.23 |
| 4,462,398 | 7/1984 | Durkan et al. | 128/200.14 |
| 4,481,944 | 11/1984 | Bunnell | 128/204.18 |
| 4,484,578 | 11/1984 | Durkan | 128/204.24 |
| 4,506,666 | 3/1985 | Durkan | 128/204.23 |
| 4,519,387 | 5/1985 | Durkan et al. | 128/204.23 |
| 4,584,996 | 4/1986 | Blum | 128/204.21 |
| 4,648,395 | 3/1987 | Sato et al. | 128/204.23 |
| 4,655,246 | 4/1987 | Philpot et al. | 137/505.11 |
| 4,686,974 | 8/1987 | Sato et al. | 128/204.23 |
| 4,705,034 | 11/1987 | Perkins | 128/204.21 |
| 4,823,788 | 4/1989 | Smith et al. | 128/205.24 |
| 4,832,014 | 5/1989 | Perkins | 128/203.12 |
| 4,873,971 | 10/1989 | Perkins | 128/201.23 |
| 5,005,570 | 4/1991 | Perkins | 128/204.23 |
| 5,038,770 | 8/1991 | Perkins | 128/204.18 |
| 5,603,315 | 2/1997 | Sasso, Jr. | 128/204.26 |

*Primary Examiner*—John G. Weiss
*Assistant Examiner*—V. Srivastava
*Attorney, Agent, or Firm*—Hudak & Shunk Co., LPA

[57] ABSTRACT

The invention relates to a respiratory gas dispensing apparatus for delivering a precise volume of respiratory gas to a patient within less than about half of an inspiratory effort comprising a source of respiratory gas in operative communication with a valve means capable of releasing a pulsed dose of respiratory gas in synchronization with the initiation of the inspiratory effort wherein the volume of the pulsed dose is constant throughout an entire pulse period. The invention further relates to a method of using the subject apparatus, and to the valve means contained in the subject apparatus.

17 Claims, 16 Drawing Sheets

METHOD AND APPARATUS FOR DISPENSING RESPIRATORY GASES

BACKGROUND

This invention pertains to a respiratory apparatus which features a means for selecting either continuous gas flow mode and pulsed gas flow mode, and further for controlling the volume of gas received by the patient while maintaining constant pressure and constant time. The apparatus also includes a fail-safe device which detects the loss of inspiratory effort and automatically initiates continuous gas flow at a variable flow rate. The invention further relates to methods for operating and using the same.

Oxygen therapy and assisted breathing devices have improved over the last several years. Common respiratory devices have been based on the delivery to the patient or user of a continuous flow of respiratory gas, most often oxygen, by transferring gas from a supply tank or supply line to a mask or cannula which is placed over the patient's mouth and nose. The volume of oxygen supplied to the patient by these devices is generally controlled by a flow regulator or meter.

These continuous flow devices, however, have been determined to be less than completely efficient in light of recent research regarding the amount of respiratory gas actually used by the patient.

Newer respiratory gas delivery devices reflect these research findings by providing oxygen or other respiratory gases to the patient as a dosed pulse of gas.

Pulse Dose on Demand oxygen delivery technology provides an arterial hemoglobin oxygen saturation as measured by pulse oximetry (SpO2) or arterial blood gas analysis equivalent to that provided by traditional continuous flow oxygen. In Pulse Dose oxygen therapy, the pulse of oxygen is delivered in the first one-third of the inspiratory effort and reaches the alveoli providing alveolar ventilation and permitting respiration or gas exchange in the lungs. Then the balance of the inspiratory volume fills the anatomical deadspace and is exhaled, not participating in the gas exchange. As an oxygen conserving device the unit is designed to take advantage of the fact that oxygen is needed only during the initial phase of inspiration.

The normal (at rest) breathing pattern allows for inhaling and exhaling in appropriate intervals. Continuous systems waste ⅔ of the oxygen they release since oxygen is supplied whether the user is inhaling or not. Pulse-dose oxygen devices sense the initiation of the user's inhalation (negative pressure) and instantly releases a short, programmed "pulse" dose at a relatively high flow rate at the leading edge of the inhalation cycle thus there is an insignificant waste of oxygen.

Current clinical practice under physicians care utilizes analysis of oxygen saturation to titrate the pulse dose equivalent to that provided by traditional continuous oxygen therapy. The lower limit tolerances for pulse dose volumes of the device are set at the minimum clinical equivalency to continuous flow.

Pulse dose oxygen systems known in the prior art are basically of two types. The first type is based on a rate-time metering of the respiratory gas flow. U.S. Pat. Nos. 4,457,303 and 4,462,398, representative of such rate-time flow metering devices, discloses systems which control of the volume of oxygen received by the patient is achieved by controlling the rate at which oxygen is allowed to flow, and the time or duration of oxygen flow for each respiratory cycle. Therefore, both the rate and the duration of flow must be precisely controlled if the dose is to be accurately measured and dispensed. Because of the small quantities of oxygen required per dose, typically about 16 cc measured at standard temperature and pressure, it is difficult to provide for the degree of accuracy of flow rate and of timing required to insure a safe dose efficiently delivered for each breath. These types of devices attempted to achieve delivery of a precise square pulse to a patient. However, in machines in use today such pulses are not achieved.

A second type of device for pulse dose oxygen supply is disclosed in U.S. Pat. No. 4,705,034, which teaches a device for administering oxygen and other respiratory gases to a patient on a pre-metered basis by temporarily storing single dose quantities of respirating gas and dispensing each dose in synchronization with the patients inspiratory cycle. The onset of inspiration is detected by a sensor which produces a signal which causes release of a single dose of gas to the patient in immediate response to the sensed signal. This type of system is a volumetric metering system and operates on the basis of known displacement of a volume of respiratory gas or oxygen. The disadvantage to this type of system is that the patient receives only a premeasured dose of respiratory gas or oxygen in an uncontrolled delivery which results in a "spike" of gas or oxygen being delivered to the patient.

The practical efficiency of prior art respiratory gas dispensing devices is easily evaluated by the control of gas delivered to a patient during a pre-set time period. This standard is documented by production of graphs showing wave forms corresponding to such delivery. For instance, a spike wave represents inconsistent delivery of volume of gas as a function of time during a single pulse. A true square wave, however, is indicative of a constant volumetric delivery over the entire pulse period.

The subject system of dispensing respiratory gases offers an improved and simplified means for dispensing an oxygen dose in synchronization with a patient's respiratory cycle over known systems. The variable volume system described and claimed hereinafter provides the advantage of a variable volume of oxygen dosed to the patient in response to the individual and specific needs of the patient.

The subject system may further incorporate an automatic recovery system, or fail-safe system, which causes the device to default to a precise volume continuous flow of oxygen to the patient automatically, without adjustment of the device, in response to failure of battery or electrical systems causing an interruption in the oxygen flow to the patient. Given the variety of volumetric settings available in the subject apparatus, and the coordination of these settings between continuous and pulsed flow delivery, the volume of the continuous flow is automatically pre-set in keeping with a doctor's instruction to coincide with the needs of the patient. Further, this system is not dependent on the patient or another third party to discover an alarm or signal indicating failure of gas flow and manually correct the system.

SUMMARY OF THE INVENTION

The invention relates to a respiratory gas dispensing apparatus for delivering a precise volume of respiratory gas to a patient within less than about half of an inspiratory effort comprising a source of respiratory gas in operative communication with a valve means capable of releasing a pulsed dose of respiratory gas in synchronization with the initiation of the inspiratory effort wherein the volume of the pulsed dose is constant throughout an entire pulse period. The invention further relates to a method of using the subject apparatus, and to the valve means contained in the subject apparatus.

DETAILED DESCRIPTION OF THE INVENTION

The subject invention pertains to a respiratory apparatus which features a means for selecting either a continuous gas flow mode or a pulsed gas flow mode, and further, for controlling the volume of gas received by the patient. The subject apparatus provides for varying the volume of flow in the continuous flow mode from about 0.25 LPM to about 6.0 LPM, and in the pulsed flow mode, from about 0.50 LPM to about 35.0 LPM. In fact, in the preferred embodiment of the subject invention eleven different flow rates are available in each of the continuous and pulsed flow modes. When operating in the pulse flow mode, the subject system apparatus delivers a continuous volume of respiratory gas at the selected flow rate over the entire pulse period, and within less than half of the inspiratory effort of the patient. Specifically, the apparatus delivers the desired volume of respiratory gas, at consistent flow rate, within the first 400 milliseconds of the inspiratory effort.

The subject apparatus further provides a failsafe feature which detects a loss of power when in the pulse mode, and automatically fails to a continuous gas flow to the patient. Given the valve design in the preferred embodiment, which provides for variable flow rate settings, a comparable flow rate is initiated in the continuous gas flow with respect to that which was preselected in the pulsed flow mode.

The invention will now be discussed with reference to the FIGURES for the convenience of the reader. Throughout the figures, like numbers have been used to designate substantially similar components.

Figure 1:
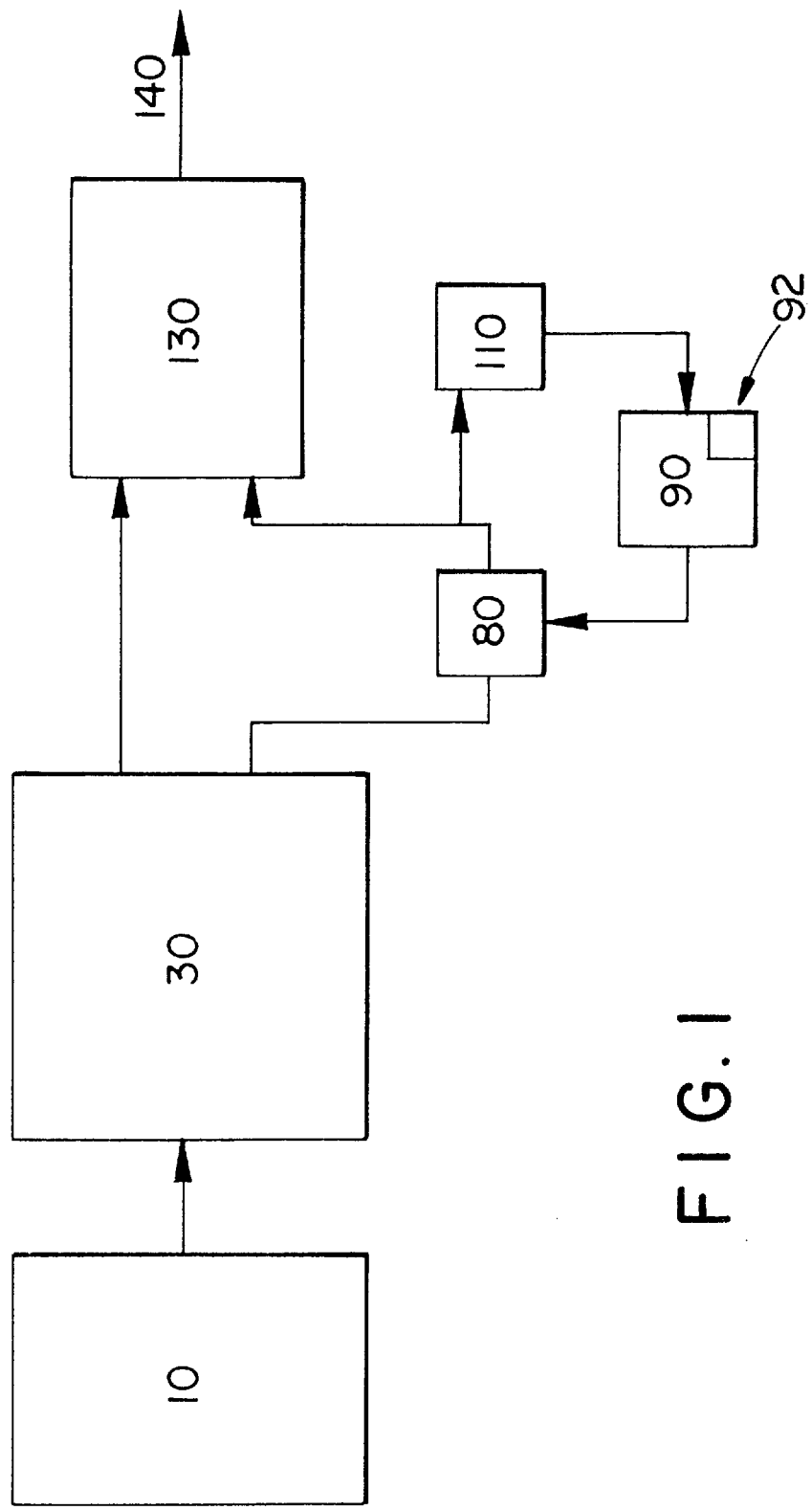
FIG. 1 is a block diagram of the respiratory gas dispensing apparatus.

FIG. 1 is a basic block flow diagram generally illustrating the subject respiratory gas delivery system. As can be seen, the system includes a source of respiratory gas 10, a valve means 30 for delivering continuous flow or pulse flow respiratory gas, a solenoid valve 80 for controlling gas flow, a sensing means 110 for sensing inspiratory effort, a printed circuit board 90 including an onboard computer 92, a mode select switch 130, and an outlet, or cannula 140 to the patient. The term "patient" as used herein is meant to include any user of the subject device.

When the source of respiratory gas 10 is a liquid, a heat exchanger 20 (See FIG. 2) may be used to vaporize the liquid into a gas suitable for delivery to the patient through the subject apparatus.

The valve means 30 may be a combination of valves for producing continuous and pulse gas flow. In the alternative, a single valve capable of delivering gas in both continuous and pulse mode may be used. It is an aspect of the invention that the valve means selected is capable of delivering gas in both continuous and pulse mode through distinct lines. As used hereinafter, the term "line" is meant to mean any fluid conveying means, such as a duct, conduit, pipe, channel, or any other closed fluid conducting device.

The sensing means may be any apparatus known to those skilled in the art which is capable of sensing the initiation of an inspiratory or negative effort. As will be seen with reference to the preferred embodiment of the invention, one such means is a mass flow sensor. The sensing means is in electrical contact with the printed circuit board which converts the sensing of a negative or inspiratory effort to an electrical signal and transmits the same to the solenoid valve, resulting in release of a precise dose or pulse of respiratory gas.

The mode select switch 130 may be a manually operated switch or an automated switch controlled by printed circuit board 90 and the on-board computer. In one embodiment, when the subject respiratory gas delivery apparatus includes the fail-safe device disclosed hereinafter, the switch is automated in order for the fail-safe feature to function properly.

Figure 2:
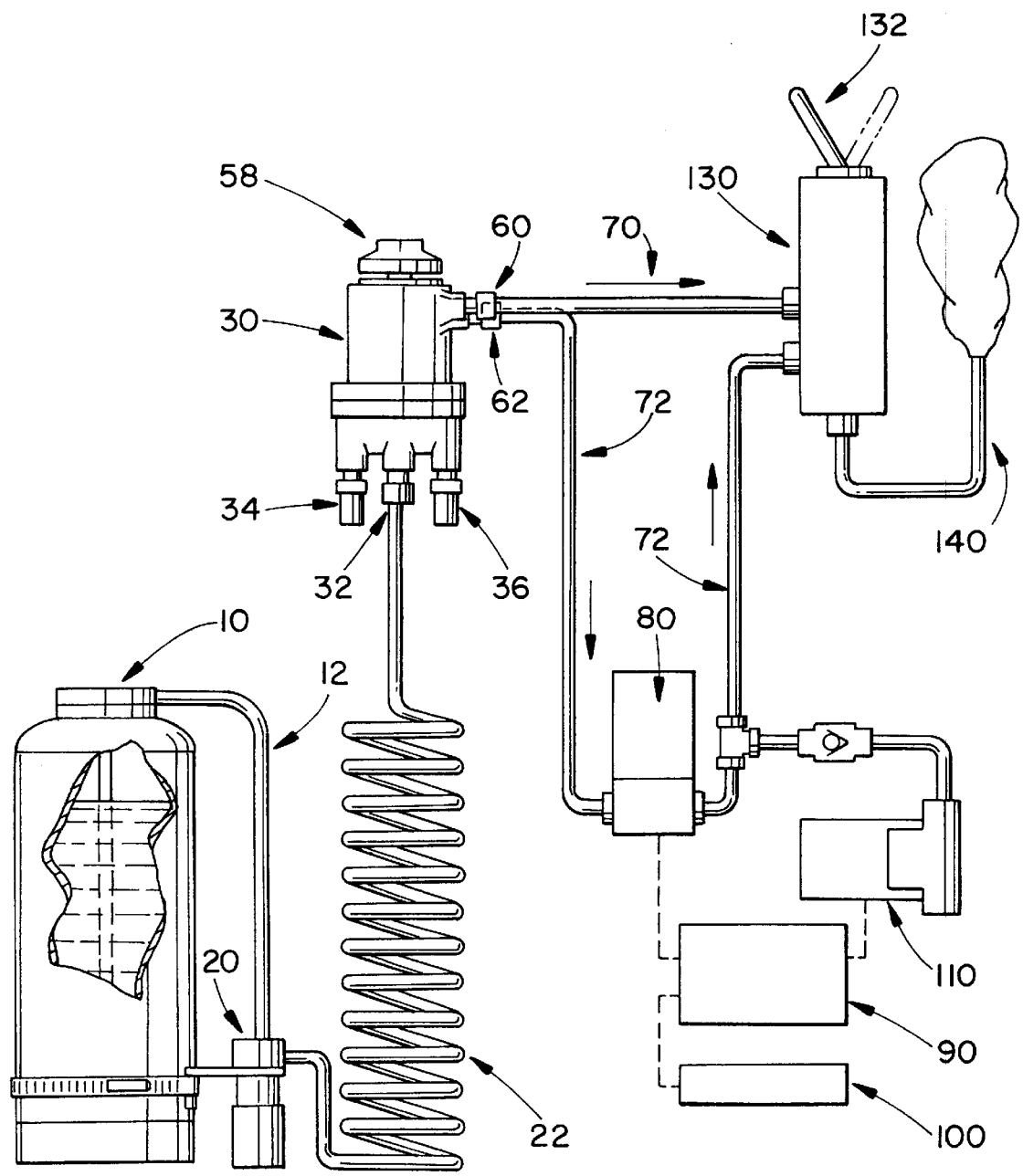
FIG. 2 is a schematic overview of the preferred embodiment of the respiratory gas dispensing apparatus.

FIG. 2 represents the preferred embodiment of the invention. In the preferred embodiment, source of gas 10 is a source of liquid oxygen. However, any respiratory gas may be supplied, therefore any reference to oxygen is equally applicable to other respiratory gases. Depending upon the particular environment of use, the source may be a portable tank, a stationary tank, or may be a permanent wall capacity device.

A fluid conducting line 12 exits supply tank 10 and carries the liquid oxygen through heat exchanger 20 to vaporize the liquid into oxygen gas. This gas is then delivered through gas conducting line 22 into flow selector valve 30 through inlet port 32. A regulated gas flow control valve of the type shown in U.S. Pat. No. 4,655,246, the disclosure of which is incorporated herein by reference, is generally suitable for use in the subject invention with changes as indicated herein below. The valve disclosed in the 4,655,246 patent comprises a regulated gas flow control valve, including a valve body having an inlet at one end for receiving gas from a supply tank or other respiratory gas source. A flow control selector knob is located at the other end of the valve body. The knob selects a preselected flow rate for delivery of gas through an outlet. The knob controls position of a rotor carrying a plurality of pre-calibrated flow control orifice inserts, the knob being rotatable but with positive detenting for orienting the rotor to permit flow only through the pre-selected orifice for delivery to the patient.

The subject valve differs from the valve disclosed in the 4,655,246 patent in a variety of ways including that it has dual outlet ports, one port designated for use in the continuous flow mode, and a second port designated for use in the pulsed flow mode. The valve of the subject invention further differs from that in the 4,655,246 patent in that the subject valve rotor has 24 orifices configured for allowing the communication of a wide range of volumetric flows of respirating gas to the patient during normal operation and emergency operation. These features of the valve used in the subject invention are fully discussed herein below.

The flow selector valve of the subject invention has, as was stated herein above, an inlet port 32 for receiving gas from a supply tank or other gas source 10, through gas conducting line 22. The flow selector valve has relief valves 34 and 36, which is an arrangement common to the valve industry for maintaining valve pressure at acceptable levels.

Gas received through inlet port 32 is immediately communicated through two of the 24 orifices in a rotatable disc 40 (See FIG. 8) within the flow selector valve 30. This disc, as well as the remaining parts of the valve, will be discussed in more detail with reference to FIGS. 3–8 in the disclosure set forth hereafter. Now then, gas is transmitted through valve 30 and then exits the valve dual outlet ports 60 and 62, only one of which is ultimately in open communication with the outlet or cannula 140 at any given time. Outlet port 60 is a low flow rate port and is designated for use in the continuous mode. Outlet port 62 is a high flow rate port used only for pulse flow dosing.

The low and high outlet ports are connected by flow lines 70 and 72 respectively to mode select switch 130. This switch allows the user to operate the device in a continuous mode or in a pulse mode, but not in both modes simultaneously. Because only one of flow lines 70,72 is in open communication with the outlet or cannula 140 at a given time, there is no danger of over oxygenation of the user or patient due to inhalation of excess pulsed air while receiving a regulated continuous flow of oxygen.

In the embodiment depicted in FIG. 2, the mode select switch 130 is a manual switch, though an automated switch may also be used. When manual, the mode select switch 130 has a toggle 132. When toggle 132 of the mode select switch 130 is in the continuous mode, or deflected to the right as shown by dotted line in FIG. 2, oxygen flows continuously through flow line 70 into cannula 140 and is received by the user or patient.

When toggle 132 of the mode select switch 130 is in the pulse mode, or deflected to the left as shown by solid line in FIG. 2, a precise dose of oxygen is pulsed through line 72 to and ultimately through cannula 140 after travelling through solenoid valve 80 and through mode select switch 130. Gas emitted in the pulse mode is received by the patient within the first 400 milliseconds of inspiration.

Figure 3:
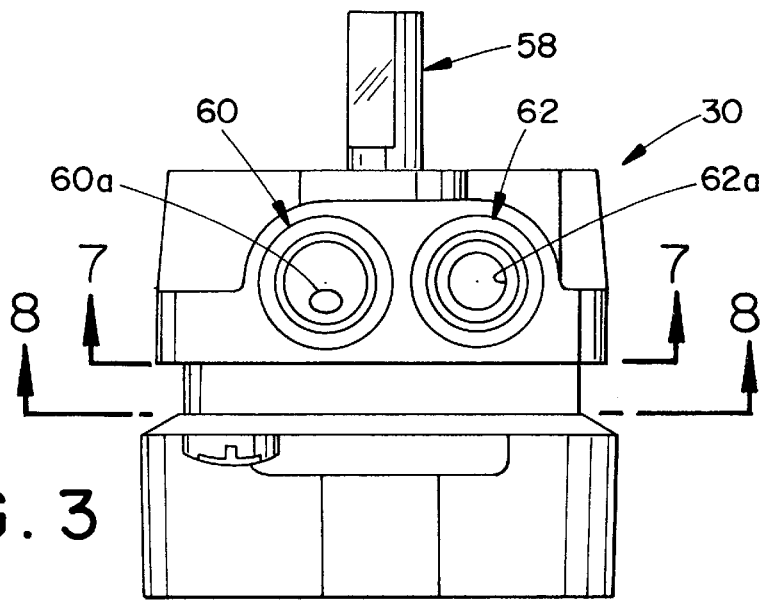
FIG. 3 is a side plan view of the flow selector valve.

The valve means used in the preferred embodiment will now be discussed with reference to FIGS. 3–8. In the preferred embodiment of the invention, the flow selector valve 30 is a dual outlet port valve capable of delivering gas to the patient in numerous different volumes and in either continuous or pulsed flow. FIG. 3 is a plan view of flow selector valve 30. Dual outlet ports 60 and 62 are shown side-by-side on the upper portion of the valve. Outlet port 60 includes a reduced opening 60a to assist in achieving its relatively low flow rate when the overall system is operating in the continuous flow mode and outlet port 62 includes an opening 62a greater than the reduced opening 60a to assist in achieving its relatively high flow rate when the overall system is operating in the pulsed flow mode.

Figure 4:
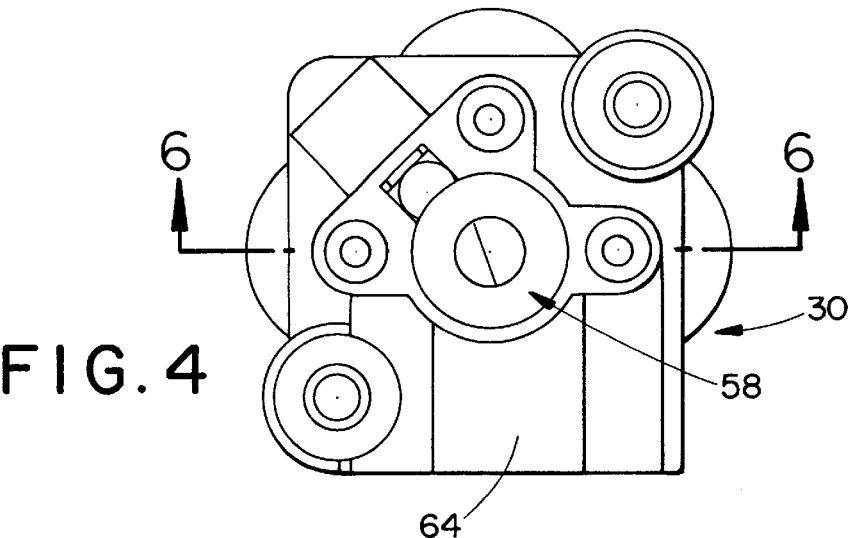
FIG. 4 is a plan view of the top of the flow selector valve.

FIG. 4 shows a top view of the valve shown in FIG. 3. Knob 58 is used to dial the appropriate volume of gas flow. Outlet ports 60 and 62 are seated in channel 64.

Figure 5:
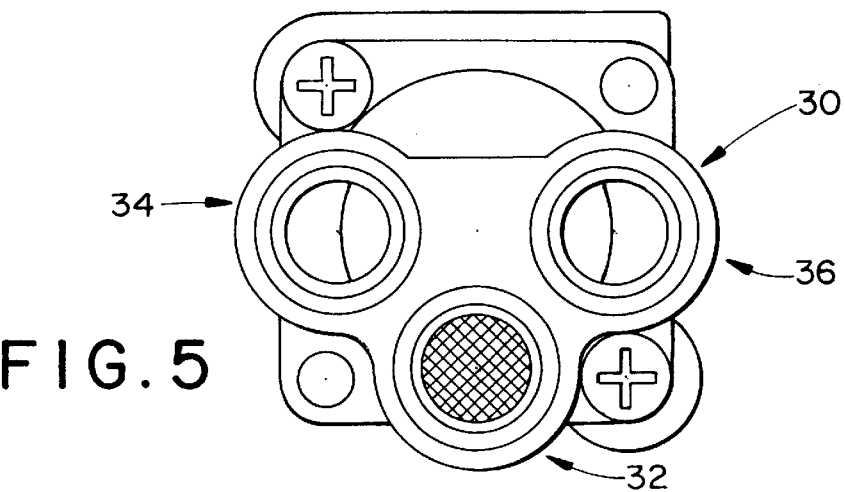
FIG. 5 is a plan view of the bottom of the flow selector valve.
Figure 6:
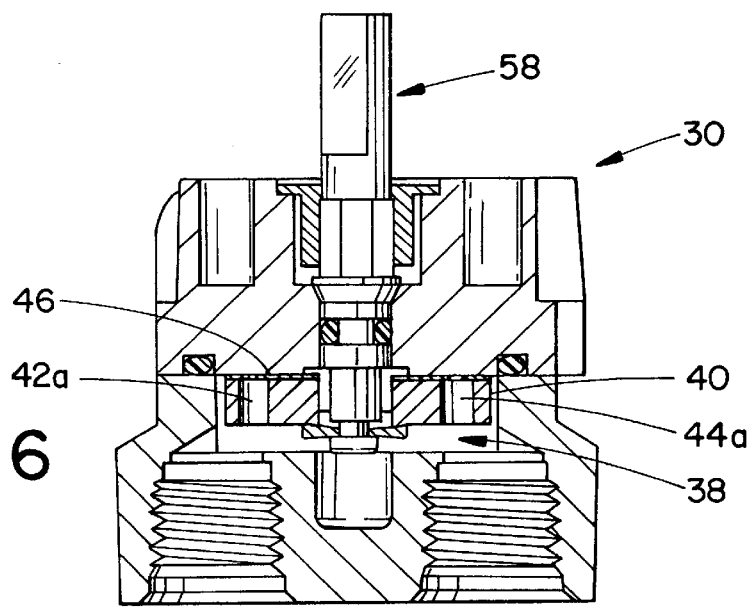
FIG. 6 is a cross-sectional view of the flow selector valve generally along line A—A of FIG. 4.
Figure 7:
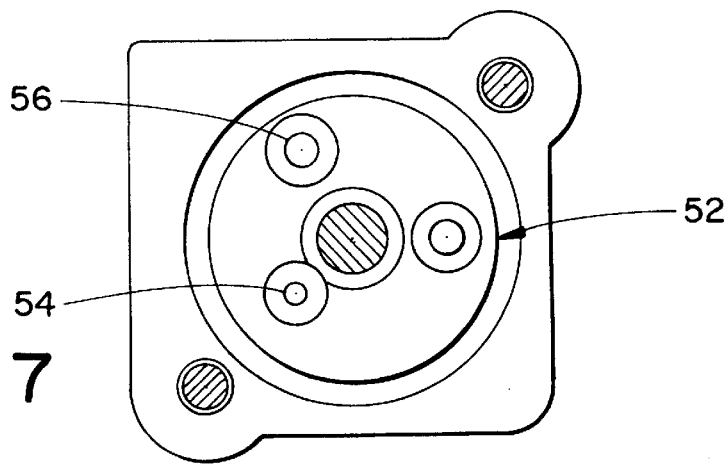
FIG. 7 is a cross-sectional view of the flow selector valve generally along line C—C of FIG. 3.
Figure 8:
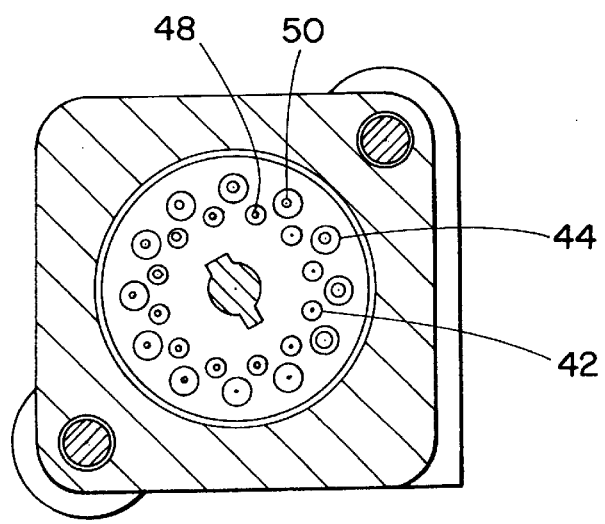
FIG. 8 is a cross-sectional view of the flow selector valve generally along line D—D of FIG. 3.

FIG. 5 is a plan view of the bottom of valve 30 showing inlet port 32 and relief valves 34 and 36. Now, in use, as air enters the flow selector valve 30 through inlet port 32, it is communicated to and evenly distributed in chamber 38 which is shown in FIG. 6 which is a cross-sectional view of the valve generally along line A—A of FIG. 4. Seated in chamber 38 is a rotatable disc 40. Disc 40, has twenty four orifices 40,42 inscribed therein which define gas communicating apertures extending from the lower surface of disc 40, seen in FIG. 8, through to the upper surface of disc 40 which abuts rotor 52, shown in FIG. 7. Two of these orifices, 42a and 44a, are seen in FIG. 6. As illustrated in FIG. 8, which is a cross-sectional view of the valve taken generally along line C—C of FIG. 3. The orifices are arranged on disc 40 in two concentric rings of twelve orifices each, the outer ring orifices 44 being of a larger overall diameter than the inner ring orifices 42. All of the orifices in inner ring 42 being the same size as all of the orifices in the outer ring 44 of the same size. The orifices are arranged in the concentric rings 42 and 44 such that when in use, a given pair of outer and inner orifices allow the same relative flow volume in continuous or pulse flow mode, i.e. if the inner orifice in communicating position allows a continuous flow of 0.25 LPM, the outer orifice in communicating position allows a pulse flow of 0.50 LPM.

In intimate contact with the top face of disc 40 is a plate 46, seen in FIG. 6, having various sized apertures therethrough, each of which coordinates with one of the orifices in disc 40. The variation in size of these apertures can be seen in FIG. 8 as openings 48, corresponding to the inner orifices 42 of disc 40, and 50, corresponding to the outer orifices 44 of disc 40. The apertures 48 and 50 in plate 46 range in size generally from about 0.003 to 0.041 inches.

When in use, plate 46 is in intimate contact with rotor 52 in the upper portion of flow selector valve 30. Rotor 52 is more clearly seen in FIG. 7, which is a cross-sectional view generally along line C—C of FIG. 3. Rotor 52 has one aperture 54 which communicates with the inner orifices 48 of the disc 40/plate 46 combination and another aperture 56 which communicates with the outer orifices 50 on the disc 40/plate 46 combination. Knob 58 allows the user to rotate disc 40, permitting flow through only one inner orifice 48 or one outer orifice 50 as it is brought into line with inner aperture 54 and outer aperture 56 on rotor 52. Positive detenting of knob 58 maintains disc 40 in the selected position with respect to rotor apertures 54 and 56. Therefore, two of the twenty-four orifices, one inner orifice and one outer orifice, are in operative communicating pairs at any given time. The various size orifices are arranged such that the communicating orifice pairs will have the same relative flow rate, thus ensuring the same relative flow type in continuous or pulse mode. Such pairs are shown in TABLE I. The full import of this arrangement will be more clearly understood by the reader with reference to FIG. 17, discussed hereinbelow.

TABLE I

| FLOW RATE COORDINATION, LPM | | | | | | | | | | | |
|---|---|---|---|---|---|---|---|---|---|---|---|
| LOW FLOW RATE | 0.25 | .050 | .075 | 1.0 | 1.5 | 2.0 | 2.5 | 3.0 | 4.0 | 5.0 | 6.0 |
| HIGH FLOW RATE | 0.50 | 1.0 | 1.5 | 2.0 | 3.0 | 4.0 | 7.5 | 10.5 | 16.0 | 25.0 | 35.0 |

Referring again to FIG. 3, aperture 54 communicates air through outlet port 60, and aperture 56 communicates air through port 62.

As was stated hereinabove, only one of outlet ports 60 and 62 is in ultimate open communication with cannula 140 at any given time. Continuous line 70 connects outlet port 60 to mode selector switch 130. Pulse flow line 72, likewise connects outlet port 62 to mode selector switch 130. When in the continuous flow mode, gas is transmitted through continuous flow line 70 to mode selector switch 130 and then on to the patient through cannula 140.

When in the pulse flow mode position, mode selector switch 130 closes continuous flow line 70 and allows air to be pulsed through pulse line 72. This is achieved in the following manner. With mode selector switch 130 in the pulse position, energy is exerted on a pin, not shown, within mode selector switch 130 which in turn causes a release of energy to circuit board 90. Switches capable of achieving this release of energy are known to those skilled in the art and therefore no further description of the operation of this switch is deemed to be necessary at this point. One type of switch which may be used to achieve the desired results is a spool switch.

Now then, because the mode selector switch 130 is in the pulse mode, printed circuit board 90 is receiving energy from battery 100, as is mass flow sensor 110.

As the patient inhales, the mass flow sensor 110, connected to the cannula 140 through line 72, senses a negative effort. Within one millisecond of sensing this negative effort, the mass flow sensor emits a signal to the printed circuit board 90 which in turn causes solenoid valve 80 to open allowing a precisely dosed pulse of gas to pass through line 72 to cannula 140 and on to the patient. Solenoid valve 80 is closed within precisely 400 milliseconds, thus ensuring that the entire amount of pulse gas reaches the patient within the first quarter to one-eighth of the inhalation.

Figure 9A:
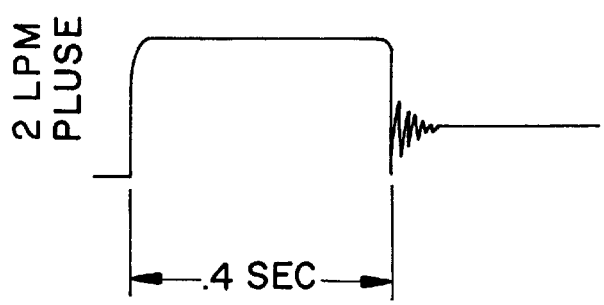
FIG. 9A is a square wave graph showing volume as a function of time from subject apparatus at 2 LPM.
Figure 9B:
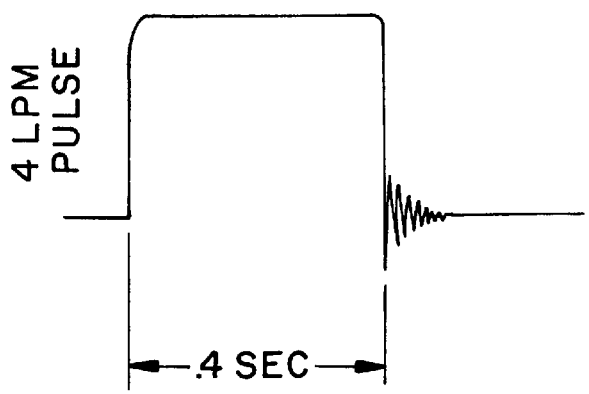
FIG. 9B is a square wave graph showing volume as a function of time from subject apparatus at 4 LPM.
Figure 9C:
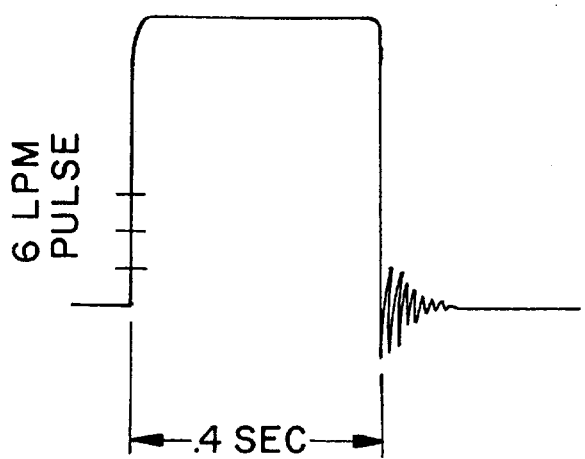
FIG. 9C is a square wave graph showing volume as a function of time from subject apparatus at 6 LPM.

This is more clearly demonstrated with reference to FIGS. 9A–9C and 10A–10C which are graphs representing the volume of oxygen received by the patient as a function of time. FIGS. 9A–9C correspond to use of the subject device as described herein above and shown in FIGS. 1–8. These graphs clearly illustrate the capability of the subject apparatus to deliver the desired volume of respiratory gas within the first 400 milliseconds of inspiration. FIG. 9A represents a flow rate of 2 LPM, corresponding to the area under the pulse, within the allotted time. With reference to FIGS. 9B and 9C, the graphs verify delivery of 4 LPM and 6 LPM respectively within the same time period. Further, these graphs demonstrate that the volume or flow rate, determined by the y axis of the graph, is consistent throughout the entire pulse period, i.e. the pulse is a "square pulse".

Figure 10A:
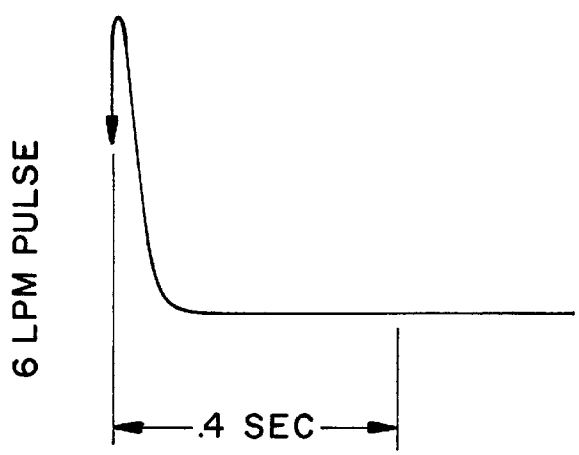
FIG. 10A is a spike wave graph showing volume of air pulsed as a function of time from Puritan Bennett apparatus at 2 LPM.
Figure 10B:
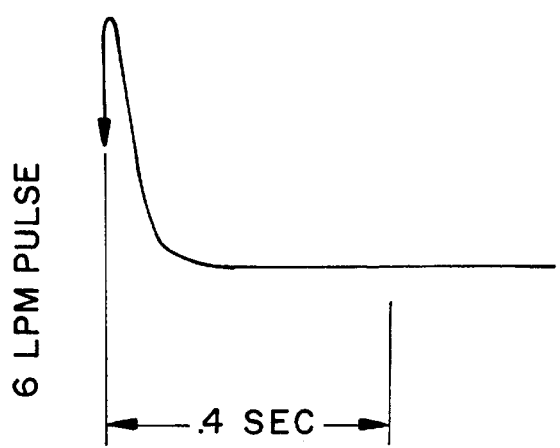
FIG. 10B is a spike wave graph showing volume of air pulsed as a function of time from Puritan Bennett apparatus at 4 LPM.
Figure 10C:
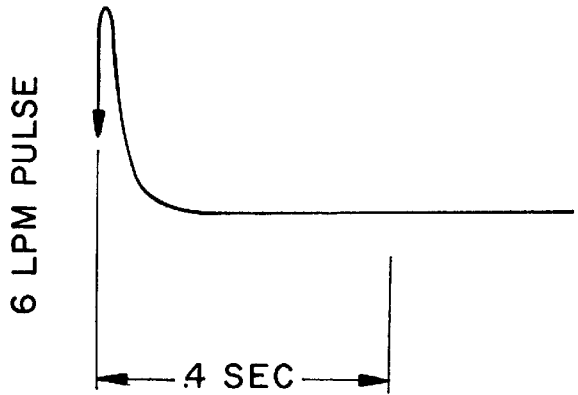
FIG. 10C is a spike wave graph showing volume of air pulsed as a function of time from Puritan Bennett apparatus at 6 LPM.

FIGS. 10A–10C illustrate the wave graph produced by a Puritan Bennett Portable Pulse apparatus in delivering the same volume as in FIGS. 9A–9C, i.e., 2 LPM, 4 LPM, and 6 LPM. This apparatus has a fixed volumetric bolus the content of which is released in response to sensing of a negative effort as the patient inhales. The bolus is constantly being refilled, therefore the patient receives the full pulse of respiratory gas contained in the bolus, shown as a spike in these graphs, and then a trailing off or constant supply, shown as a downward slope to a flat line after the spike. It will be appreciated by the skilled artisan that the volume of respiratory gas delivered to the patient varies over a single pulse period due to the spike. Further, since the bolus is of a set volume when it is necessary to deliver higher flow rate such as 6 LPM (See FIG. 10C), the patient will not receive the necessary amount of oxygen in the 400 millisecond time period. Obviously, this system also is less efficient in oxygen conservation due to the trailing effect experienced during bolus refill.

Figure 11A:
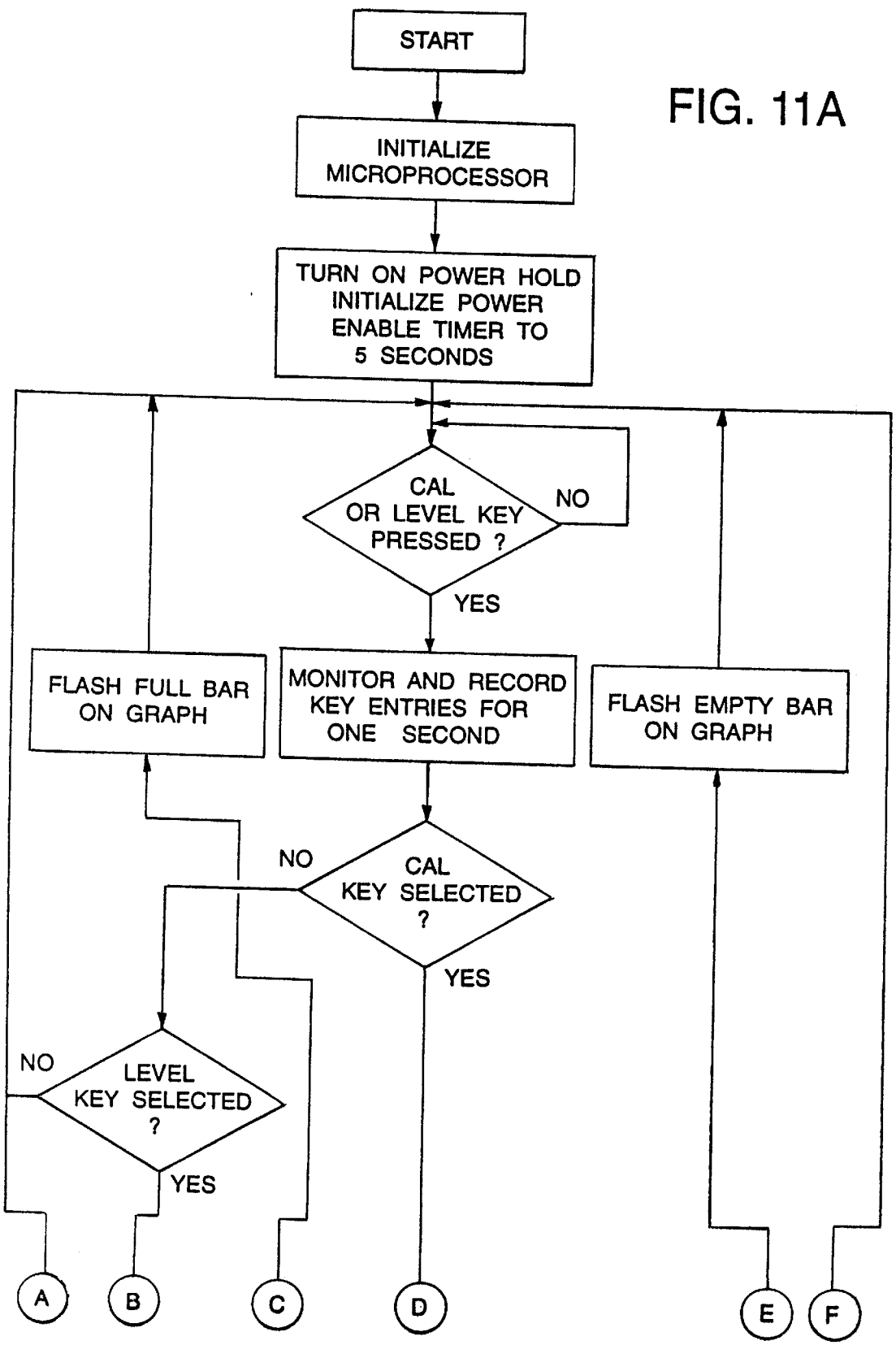
FIG. 11A is a flow chart for respiratory gas pulsed control.
Figure 11B:
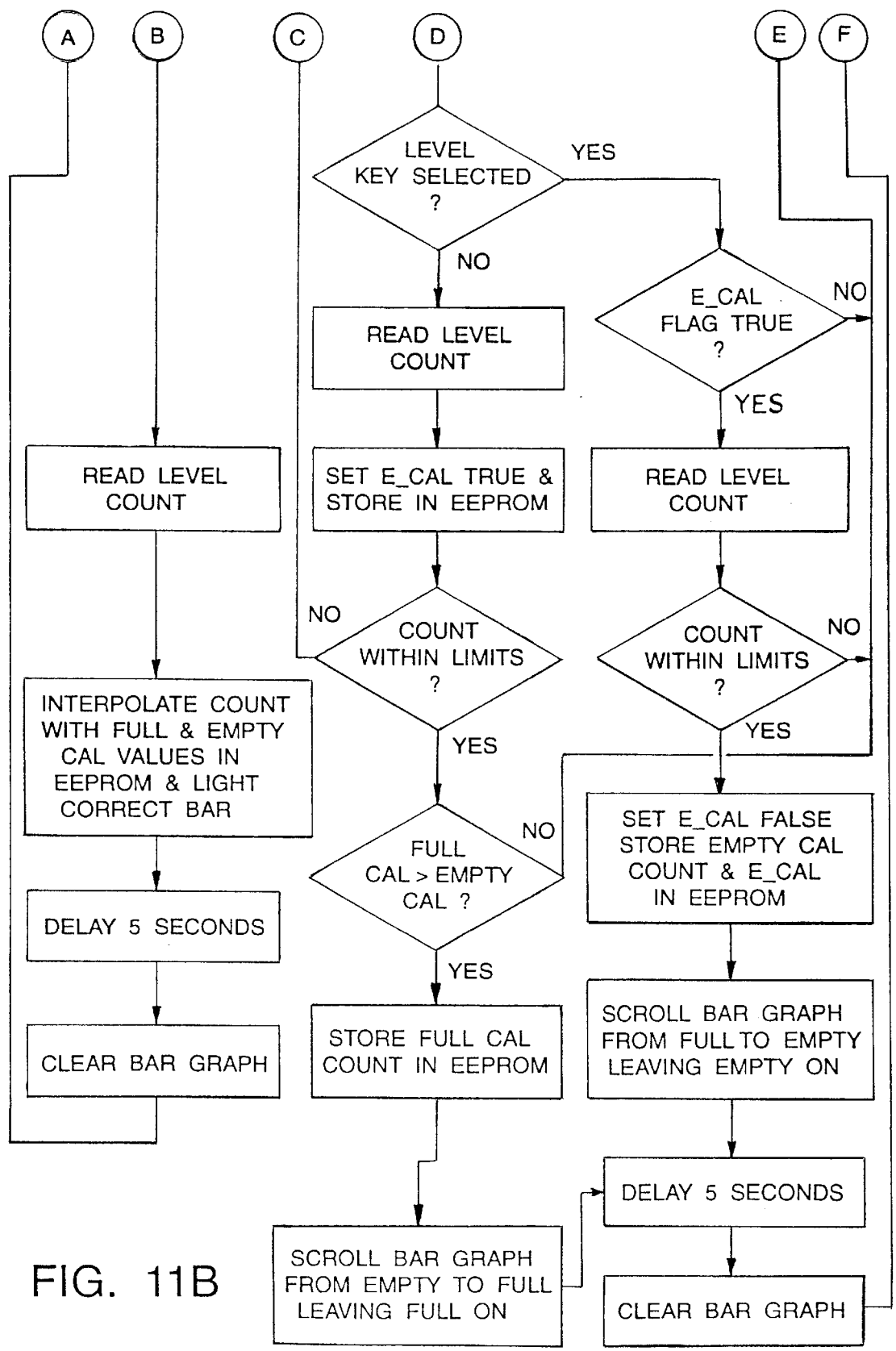
FIG. 11B is a flow chart for respiratory gas pulsed control continued from FIG. 11A.
Figure 12A:
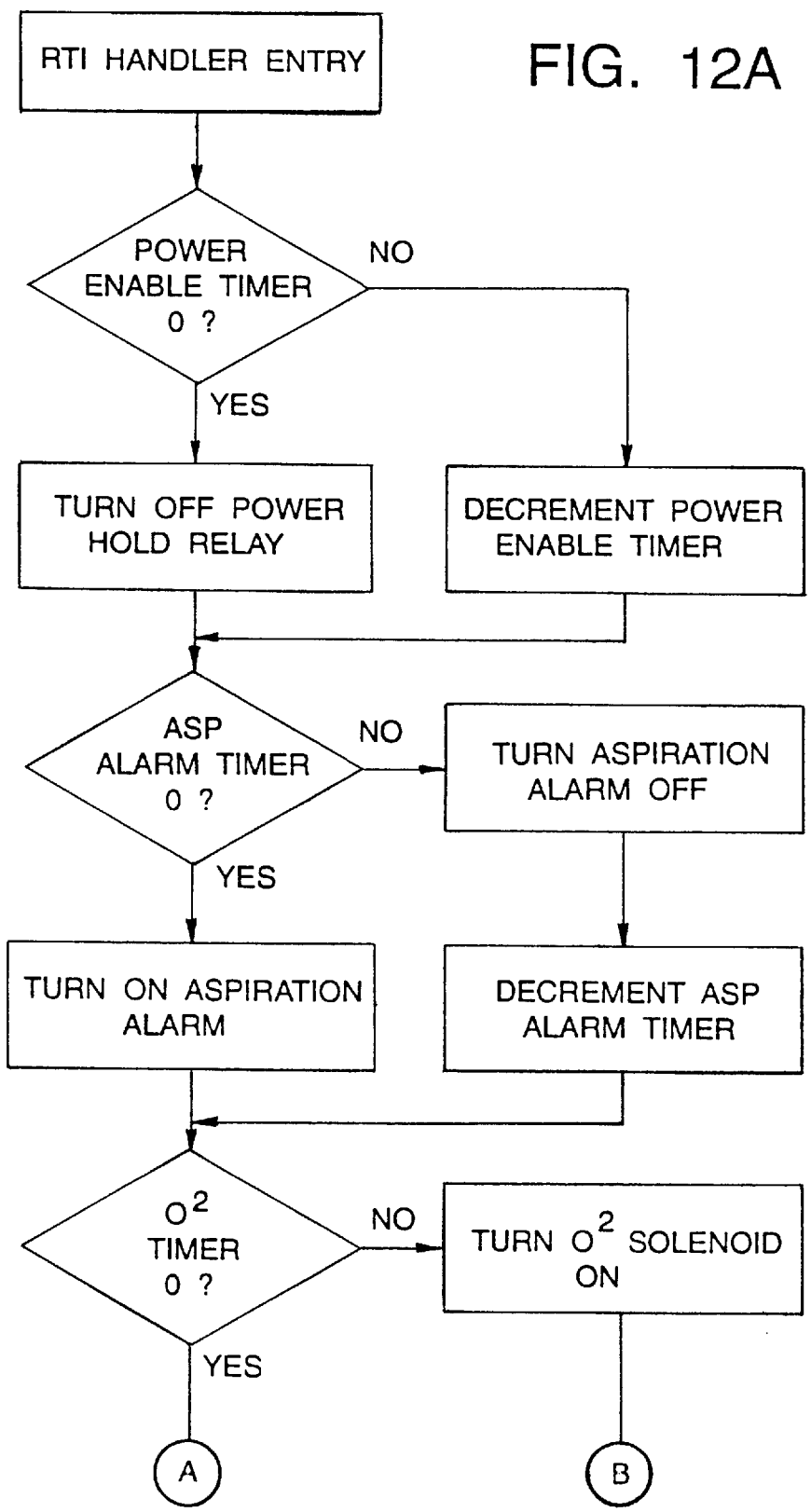
FIG. 12A is a flow chart for real time interrupt processing in respiratory gas pulsed control.
Figure 12B:
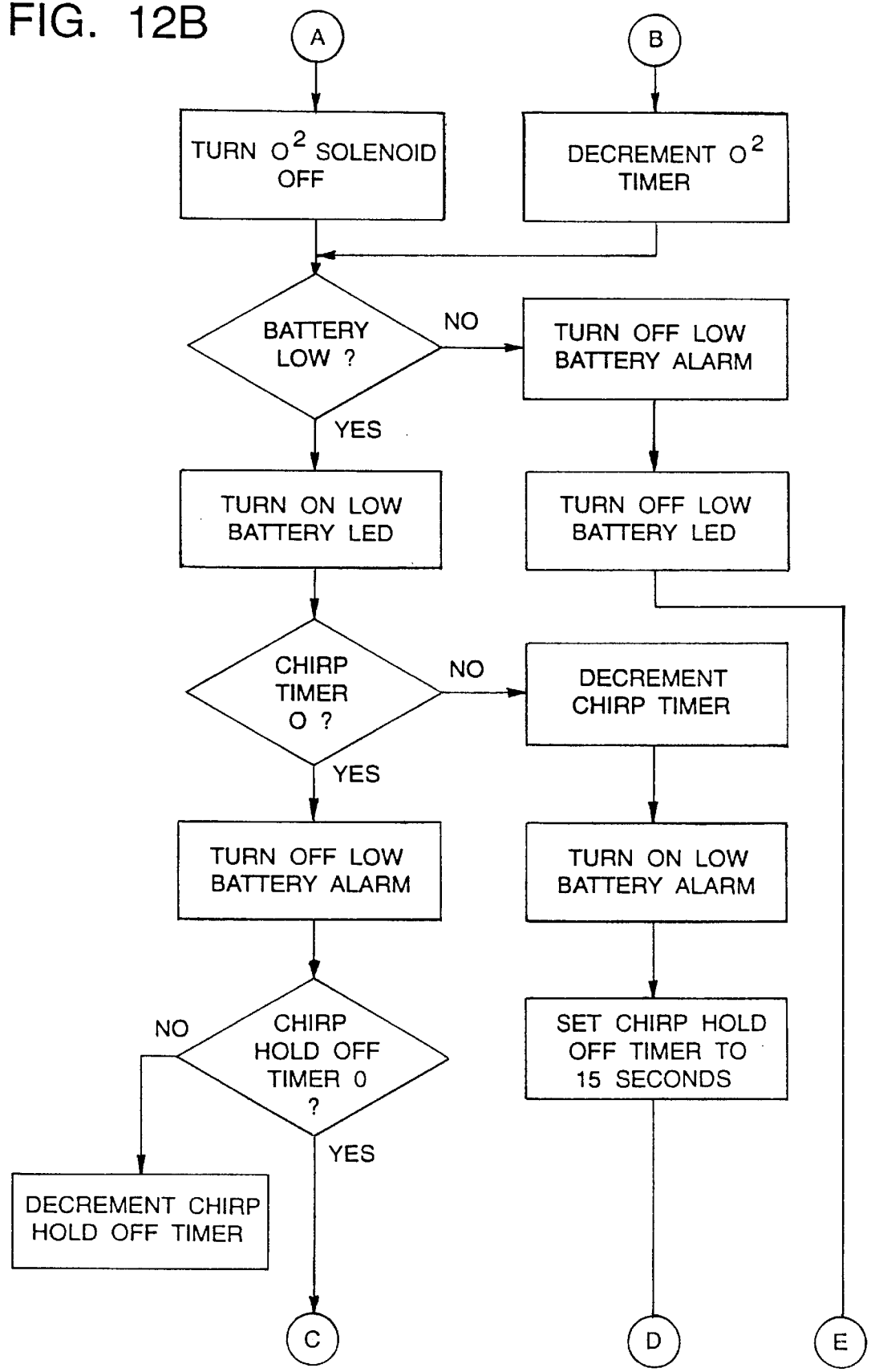
FIG. 12B is a flow chart for real time interrupt processing in respiratory gas pulsed control continued from FIG. 12A.
Figure 12C:
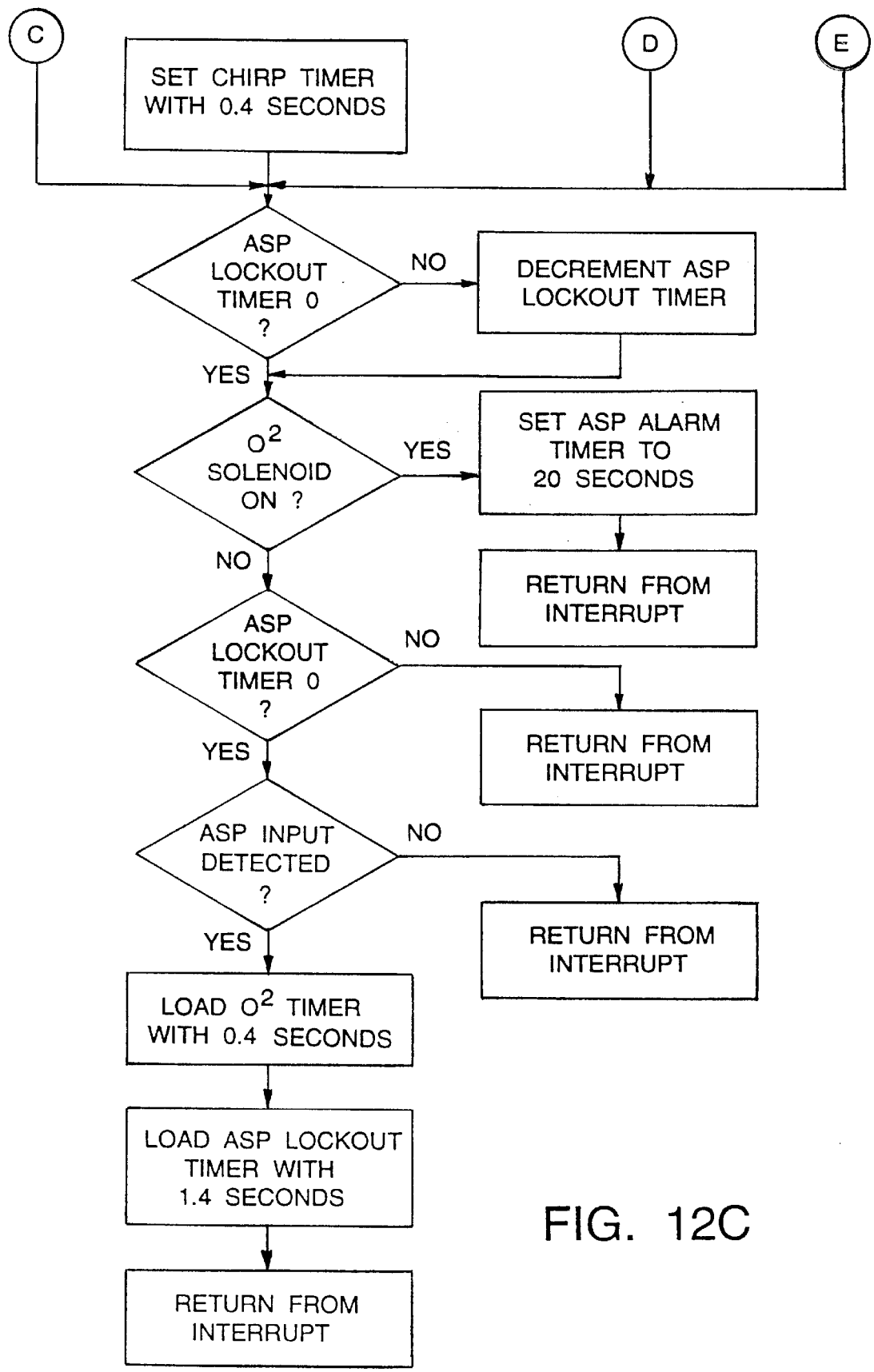
FIG. 12C is a flow chart for real time interrupt processing in respiratory gas pulsed control continued from FIG. 12B.
Figure 13:
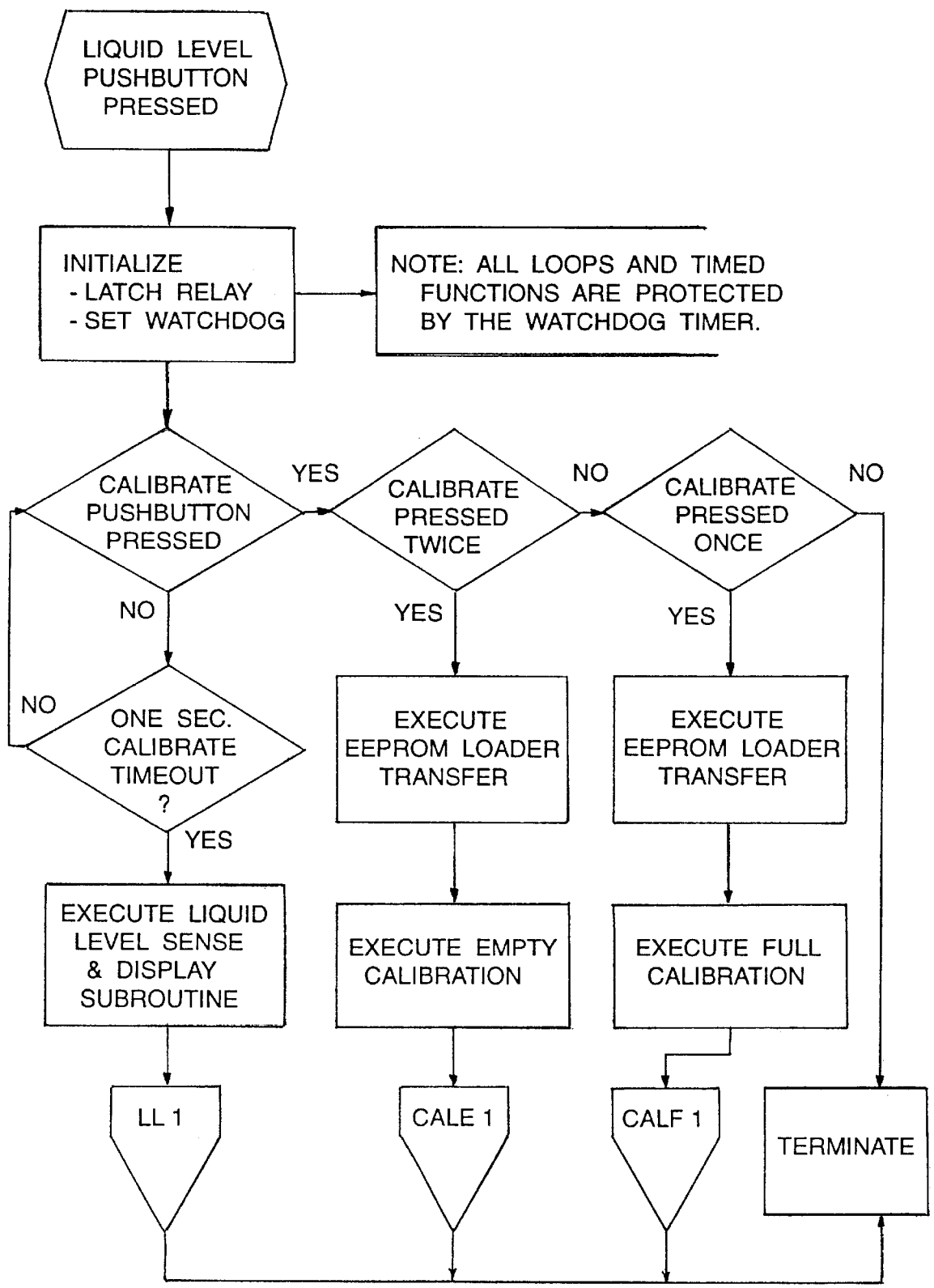
FIG. 13 is a flow chart for level sense and display.
Figure 14:
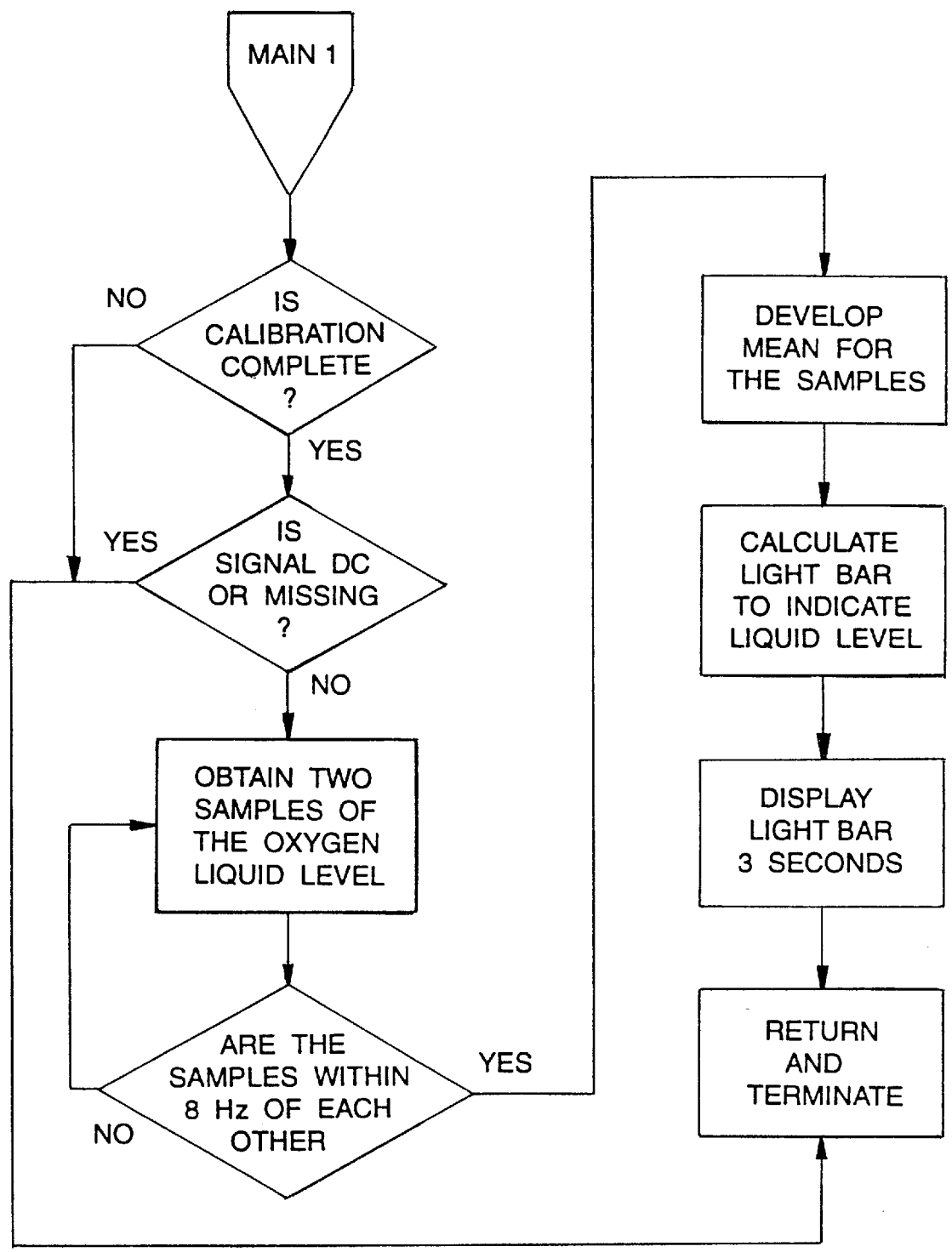
FIG. 14 is a flow chart for liquid level sense and display.
Figure 15:
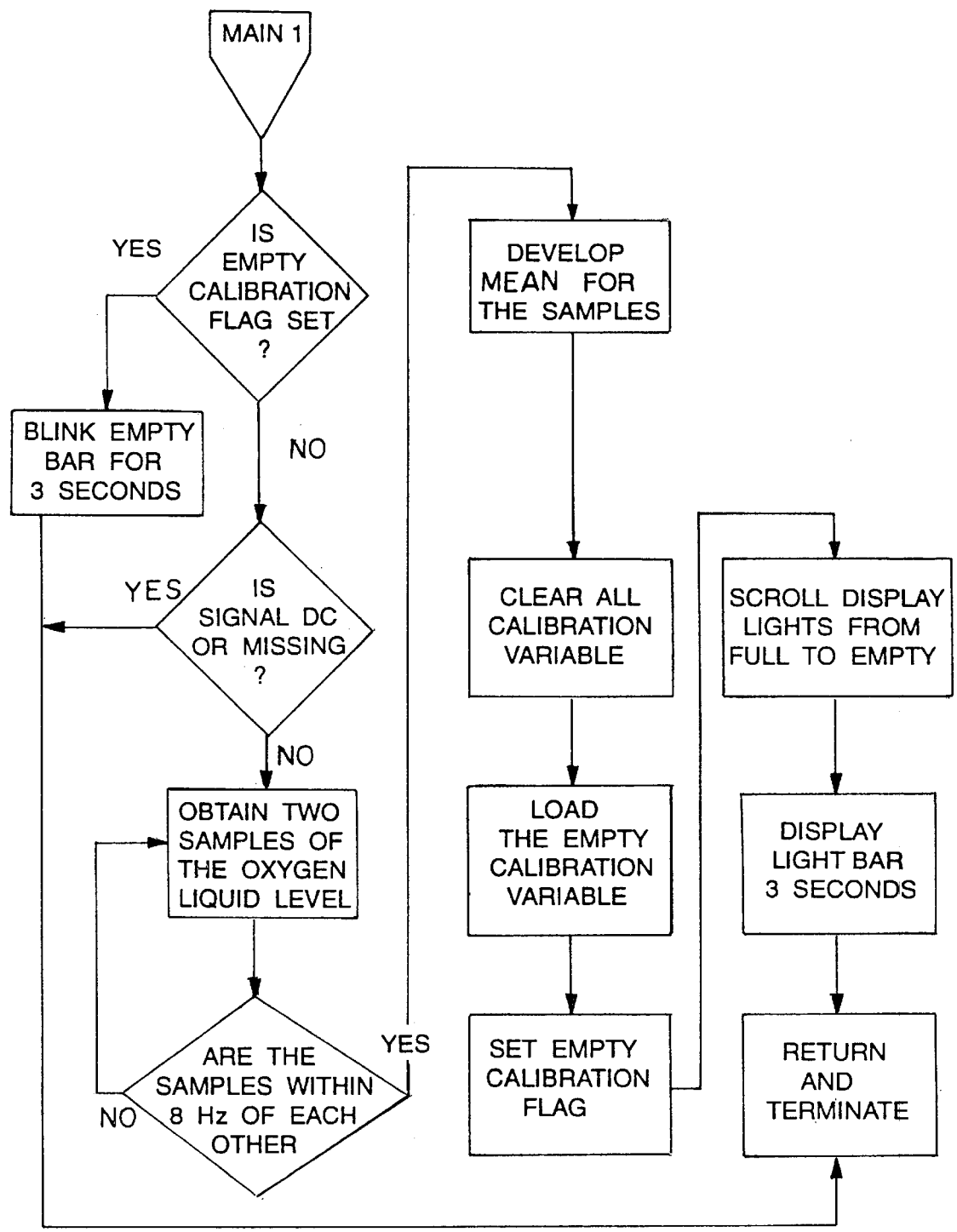
FIG. 15 is a flow chart for empty calibration.
Figure 16:
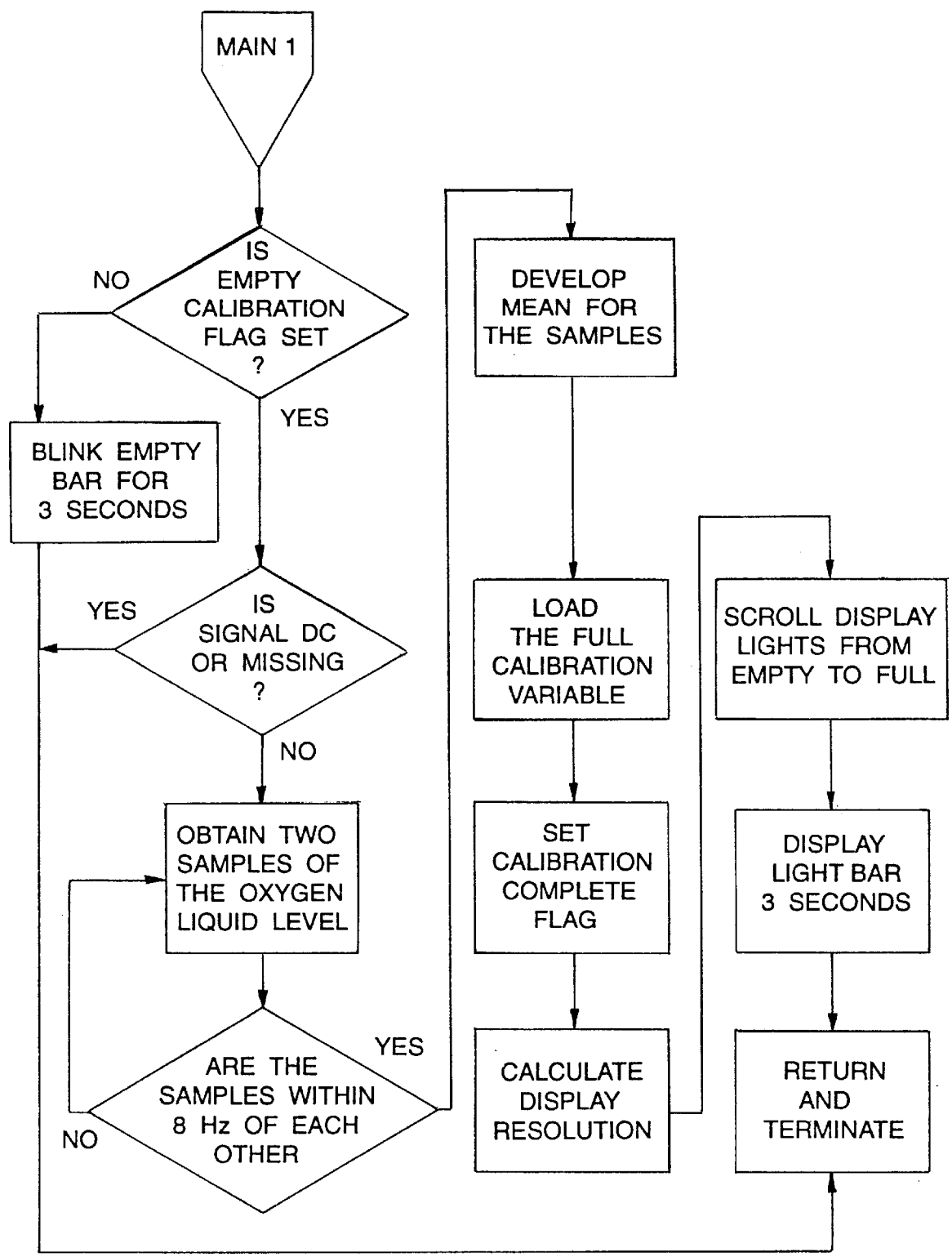
FIG. 16 is a flow chart for full calibration.

Printed circuit board 90 includes an onboard computer 92. The computer has control software which includes an overall control program, as shown generally in FIGS. 11A–11B. Other operations maintained by the computer 92 are a real time interrupt program, such as that shown generally at FIGS. 12A–12C for controlling inspiration and battery operations. Further, the computer controls a level sense and display mainline program, such as that shown generally at FIG. 13, a liquid level sense and display program, such as that shown generally at FIG. 14, an empty calibration program, such as that shown generally at FIG. 15, and a full calibration program, such as that shown generally at FIG. 16.

Figure 17:
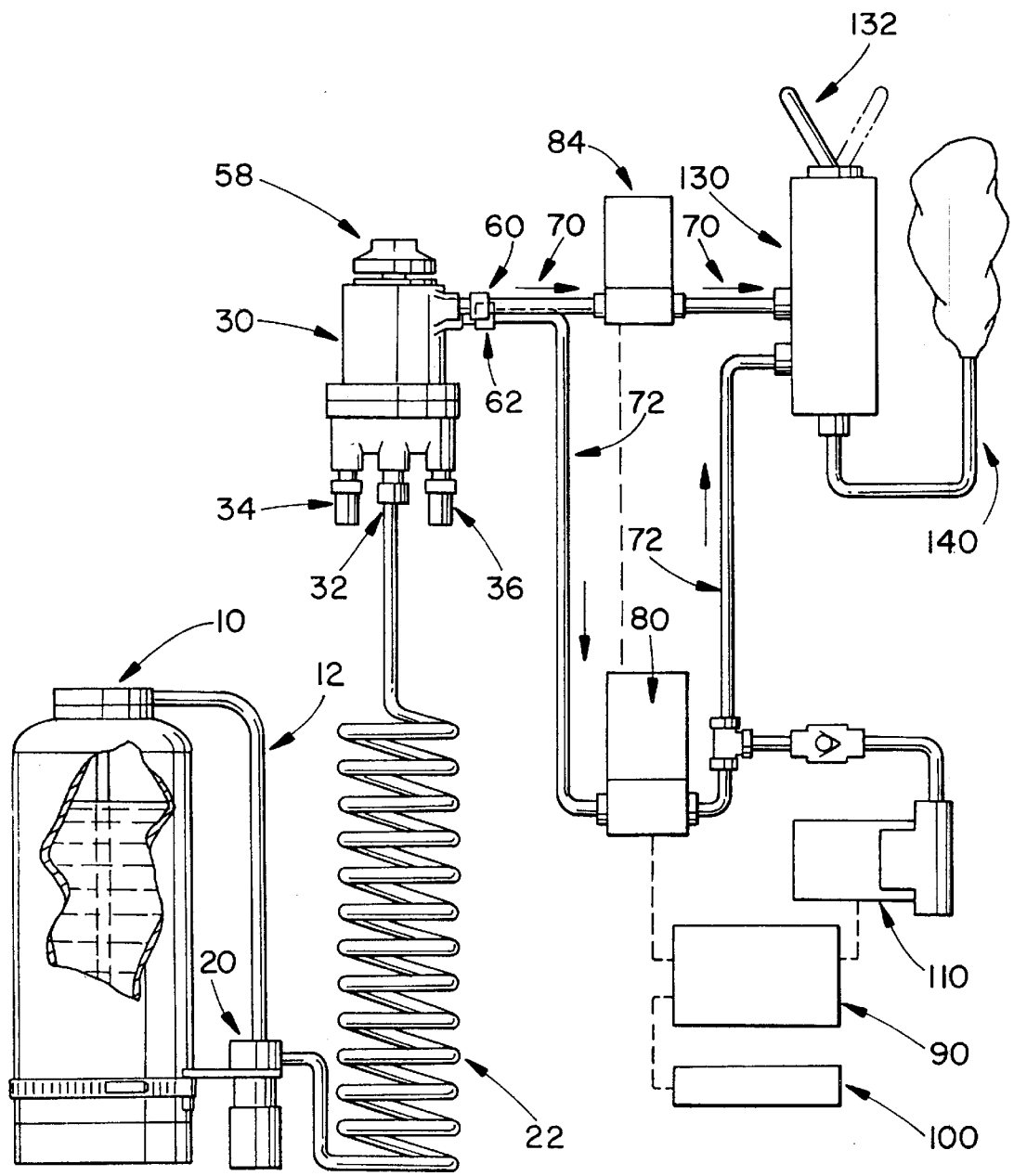
FIG. 17 is a schematic overview of an embodiment of the fail-safe respiratory gas dispensing apparatus.

In the subject device, a fail-safe system is supplied through which the device itself defaults to a continuous gas flow mode upon failure of the power supply operating the subject apparatus in the pulse flow mode. FIG. 17, represents another embodiment of the subject invention which includes the fail-safe feature as part of the respiratory gas delivery apparatus. In this embodiment, continuous flow line 70 has a solenoid valve 84 which is controlled by printed circuit board 90 and powered, therefore, by batter 100. In use, power is used to maintain the solenoid valve 84 in the closed position, allowing flow of pulsed air through line 72 as disclosed hereinabove. If the power supply of the apparatus fails, solenoid valve 80 will remain in the closed position due to lack of power. In the same manner, solenoid valve 84 will be left open due to lack of power, thereby permitting delivery of a continuous flow of gas to the patient. As was described hereinabove, the continuous flow rate will be in keeping with the pulse flow rate the patient was receiving prior to the power failure. Specifically, the system is calibrated to a timing sequence specific to the breathing of the individual user. For instance, the system may be calibrated to a 20 second time interval, during which time 3 equally spaced breaths, approximately six seconds apart, of the selected pulse size and shape are automatically delivered. If the system experiences a loss of power or computer malfunction, the pulse mode is disengaged and the continuous mode engaged. The device, due to the variation in volume provided by using the flow selector valve which is the subject hereof, offers the advantage of delivering a precise dose of respiratory gas even in the continuous flow mode by setting the selector to the prescribed volume.

Although the foregoing includes a description of the best mode contemplated for carrying out the subject invention, various modifications are contemplated. As modifications could be made in the constructions herein described and illustrated without departing from the scope of the invention, it is intended that all matter contained in the foregoing description, including the drawings referred to therein, shall be interpreted as illustrative rather than limiting.

What is claimed is:

1. A method for delivering a precise dose of respiratory gas upon initiation of an inspiratory effort and within less than half of the inspiratory effort comprising:

sensing a negative effort corresponding to the initiation of inspiration in a sensing means;

converting the sensed negative effort to an electrical signal;

transmitting the electrical signal to a solenoid valve positioned to control a flow of respiratory gas;

opening the solenoid valve in response to receipt of the electrical signal for an amount of time equal to less than half of the duration of the inspiratory effort; and delivering the dose of respiratory gas to a patient, while the solenoid valve is open, at a desired volume and at a constant flow rate.

2. A respiratory gas dispensing apparatus comprising:

a respiratory gas source for delivering respiratory gas;

a valve means for receiving the respiratory gas from the respiratory gas source, the valve means being operable in a continuous or a pulsed flow mode and having multiple apertures of varying sizes for precisely controlling flow volume of the respiratory gas wherein the valve means includes dual outlet ports, one being operable in the continuous flow mode, and one being operable in a pulsed flow mode;

a switch for selecting one of the continuous or pulse flow modes; and an outlet for transmitting the respiratory gas to a patient at a selected flow volume.

3. The respiratory gas dispensing apparatus of claim 2 wherein the respiratory gas source is a portable tank containing the respiratory gas.

4. The respiratory gas dispensing apparatus of claim 2 wherein the valve means includes a disc having two concentric rings of apertures of varying sizes, the apertures of one ring communicating air through the continuous flow mode outlet, and the apertures of the second ring communicating air through the pulsed flow mode outlet.

5. The respiratory gas dispensing apparatus of claim 4 wherein the disc is rotatable by a knob to bring only one aperture into open communication with each outlet port.

6. The respiratory gas dispensing apparatus of claim 2 wherein the switch is a manually operated switch.

7. The respiratory gas dispensing apparatus of claim 2 wherein the switch is an electrically operated switch.

8. A valve apparatus for dispensing respiratory gas in a continuous flow mode or a pulse flow mode comprising:

an inlet port at one end of the valve for receiving the respiratory gas from a respiratory gas source;

a rotatable disc located above the inlet port and in open communication therewith the disc having concentric rings of multiple orifices of varying size which extend from the bottom surface of the disc through to the top surface of the disc;

a rotor in intimate contact with the top surface of the disc, the rotor having one aperture inscribed therein for receiving respiratory gas from one of the orifices in each concentric ring;

a knob, at the end of the valve opposite the inlet port, which when turned causes rotation of the rotatable disc with positive detenting;

and two outlet ports through which respiratory gas may exit the valve apparatus, each outlet port being in transmitting communication with only one aperture in the rotor, and one outlet port operating to transmit respiratory gas in the continuous flow mode and one outlet port operating to transmit respiratory gas in the pulsed flow mode.

9. The valve apparatus of claim 8 wherein the rotatable disc has 24 orifices.

10. The valve apparatus of claim 9 wherein the 24 orifices are arranged in two concentric rings of 12 orifices each.

11. The valve apparatus of claim 10 wherein the inner concentric ring orifices vary in size to permit a flow rate of 0.25 LPM to 6.0 LPM, and the outer concentric ring orifices vary in size to permit a flow rate of from 0.50 LPM to 35.0 LPM.

12. A respiratory gas dispensing apparatus comprising:

a respiratory gas source;

a valve means for receiving respiratory gas from the respiratory gas source, the valve means having two outlet ports, one of which is connected to a first gas line, and another of which is connected to a second gas line;

the first gas line transmitting respiratory gas in a continuous manner to the patient;

the second gas line transmitting respiratory gas in a pulsed manner to the patient;

a sensing means for sensing a negative effort caused by the initiation of an inspiration by the patient;

a printed circuit board for converting the sensed negative effort into an electrical signal, and transmitting the electrical signal to a solenoid valve;

the solenoid valve suitable for opening the second gas line for a predetermined period of time in response to receipt of the electrical signal;

a switch means for opening only one of the first gas line or the second gas line at a given time;

and an outlet line for receiving respiratory gas from the opened first gas line or second gas line, and transmitting the respiratory gas to the patient.

13. The respiratory gas dispensing apparatus according to claim 12 wherein the respiratory gas source is a tank of liquid oxygen and the apparatus further includes a heat exchanger device for vaporizing the liquid oxygen to a gaseous state.

14. The respiratory gas dispensing apparatus according to claim 12 wherein the pulse of respiratory gas, which is emitted from the second gas line, has a constant volume over the entire predetermined time period.

15. The respiratory gas dispensing apparatus of claim 12 wherein the apparatus further includes a solenoid valve positioned in the first gas line, powered by the printed circuit board, which is maintained in a closed position when the apparatus is transmitting respiratory gas through the second gas line, but which is opened upon failure of the printed circuit board creating the pulsed flow to allow an automatic continous flow of respiratory gas to the patient.

16. The respiratory gas dispensing apparatus of claim 12 wherein the printed circuit board includes an onboard computer.

17. The respiratory gas dispensing apparatus of claim 12 wherein the valve means includes a means for varying the volume of gas flow.

* * * * *